(12) United States Patent
Suyker et al.

(10) Patent No.: US 6,966,917 B1
(45) Date of Patent: Nov. 22, 2005

(54) DEFORMABLE CONNECTOR FOR MECHANICALLY CONNECTING HOLLOW STRUCTURES

(75) Inventors: Wilhelmus Joseph Leonardus Suyker, Zwolle (NL); Paulus Thomas Wilhelmus Suyker, Amsterdam (NL)

(73) Assignee: Innovation Interventional Technologies B.V., Amsterdam (NL)

( * ) Notice: Subject to any disclaimer, the term of this patent is extended or adjusted under 35 U.S.C. 154(b) by 414 days.

(21) Appl. No.: 09/708,617

(22) Filed: Nov. 9, 2000

(51) Int. Cl.$^7$ ............................................. A61B 17/04
(52) U.S. Cl. ....................... 606/148; 606/151; 606/153; 606/198; 606/213; 606/219
(58) Field of Search ................... 606/148, 150–156, 606/213, 215, 216, 219, 221, 198, 139, 140, 606/419; 623/1.14, 1.13, 1.21; 604/104; 227/175.1, 179.1, 181.1, 901, 902

(56) References Cited

U.S. PATENT DOCUMENTS

| | | |
|---|---|---|
| 1,251,258 A | 12/1917 | Magill |
| 1,756,670 A | 4/1930 | Treat |
| 1,918,890 A | 7/1933 | Bacon |
| 2,434,030 A | 1/1948 | Yeomans |
| 2,453,056 A | 11/1948 | Zack |
| 2,707,783 A | 5/1955 | Sullivan |
| 3,040,748 A | 6/1962 | Klein et al. |
| 3,080,564 A | 3/1963 | Strekopitov et al. |
| 3,193,165 A | 7/1965 | Akhalaya et al. |
| 3,217,557 A | 11/1965 | Martinol |
| 3,252,643 A | 5/1966 | Strekopytov et al. |
| 3,254,650 A | 6/1966 | Collito |
| 3,254,651 A | 6/1966 | Collito |
| 3,269,630 A | 8/1966 | Fleicher |
| 3,388,847 A | 6/1968 | Kasulin et al. |
| 3,452,615 A | 7/1969 | Gregory |
| 3,494,533 A | 2/1970 | Green et al. |
| 3,519,187 A | 7/1970 | Kapitanov |
| 3,552,626 A | 1/1971 | Astafiev et al. |
| 3,570,497 A | 3/1971 | Lemole |
| 3,589,589 A | 6/1971 | Akopov |
| 3,593,903 A | 7/1971 | Astafiev et al. |
| 3,638,652 A | 2/1972 | Kelley |
| 3,657,744 A | 4/1972 | Ersek |
| 3,692,224 A | 9/1972 | Astafiev et al. |
| 3,774,615 A | 11/1973 | Lim et al. |
| 3,805,793 A | 4/1974 | Wright |
| 3,908,662 A | 9/1975 | Razgulov et al. |

(Continued)

FOREIGN PATENT DOCUMENTS

DE   28 22 603 A1   5/1978

(Continued)

OTHER PUBLICATIONS

Androsov, "New Method of Surgical Treatment of Blood Vessel Lesions," Arch. Surg. 1956;73:262-265.

(Continued)

*Primary Examiner*—Henry Bennett
*Assistant Examiner*—Andrea M. Ragonese
(74) *Attorney, Agent, or Firm*—Knoble Yoshida & Dunleavy, LLC

(57) ABSTRACT

A connector, applicator and method for mechanically connecting hollow structures, in particular small blood vessels, in order to make an anastomosis. The connector incorporates various features to create a reliable engagement with the vessel walls to make a good connection thereof.

The connector includes knife members to make an arteriotomy in and punch a hole in one of the vessel walls, an expansion portion to cause a large expansion with a minimum profile, and anvil members to reliably bring the staple-like elements to the joining position.

29 Claims, 9 Drawing Sheets

U.S. PATENT DOCUMENTS

| | | | |
|---|---|---|---|
| 4,076,162 A | 2/1978 | Kapitanov et al. | |
| 4,140,126 A | 2/1979 | Choudhury | |
| 4,166,466 A | 9/1979 | Jarvik | |
| 4,214,587 A | 7/1980 | Sakura, Jr. | |
| 4,233,981 A | 11/1980 | Schomacher | |
| 4,304,236 A | 12/1981 | Conta et al. | |
| 4,319,576 A | 3/1982 | Rothfuss | |
| 4,325,376 A | 4/1982 | Klieman et al. | |
| 4,350,160 A | 9/1982 | Koslesov et al. | |
| 4,352,358 A | 10/1982 | Angelchik | |
| 4,366,819 A | 1/1983 | Kaster | |
| 4,368,736 A | 1/1983 | Kaster | |
| 4,466,436 A | 8/1984 | Lee | |
| 4,505,414 A | 3/1985 | Filipi | 227/19 |
| 4,523,592 A | 6/1985 | Daniel | |
| 4,553,542 A | 11/1985 | Schenck et al. | |
| 4,573,468 A | 3/1986 | Conta et al. | |
| 4,576,167 A | 3/1986 | Noiles | |
| 4,586,503 A | 5/1986 | Kirsch et al. | |
| 4,592,354 A | 6/1986 | Rothfuss | |
| 4,593,693 A | 6/1986 | Schenck | |
| 4,603,693 A | 8/1986 | Conta et al. | |
| 4,607,637 A | 8/1986 | Berggren et al. | |
| 4,624,255 A | 11/1986 | Schenck et al. | |
| 4,624,257 A | 11/1986 | Berggren et al. | |
| 4,646,745 A | 3/1987 | Noiles | |
| 4,657,019 A | 4/1987 | Walsh et al. | |
| 4,665,906 A | 5/1987 | Jervis | |
| 4,681,110 A | 7/1987 | Wiktor | |
| 4,700,703 A | 10/1987 | Resnick et al. | 128/334 |
| 4,703,887 A | 11/1987 | Clanton et al. | |
| 4,747,407 A | 5/1988 | Liu et al. | |
| 4,800,882 A | 1/1989 | Gianturco | |
| 4,872,874 A | 10/1989 | Taheri | |
| 4,907,591 A | 3/1990 | Vasconcellos et al. | |
| 4,917,087 A | 4/1990 | Walsh et al. | |
| 4,917,090 A | 4/1990 | Berggren et al. | |
| 4,917,091 A | 4/1990 | Berggren et al. | |
| 4,957,499 A | 9/1990 | Lipatov et al. | |
| 5,035,702 A | 7/1991 | Taheri | |
| 5,064,435 A | 11/1991 | Porter | |
| 5,102,417 A | 4/1992 | Palmaz | |
| 5,104,399 A | 4/1992 | Lazarus | |
| 5,119,983 A | 6/1992 | Green et al. | |
| 5,177,112 A | 1/1993 | Horn | 514/654 |
| 5,188,638 A | 2/1993 | Tzakis | |
| 5,197,649 A | 3/1993 | Bessler et al. | |
| 5,234,447 A | 8/1993 | Kaster et al. | |
| 5,234,456 A | 8/1993 | Silvestrini | |
| 5,242,457 A | 9/1993 | Akopov et al. | |
| 5,250,058 A | 10/1993 | Miller et al. | |
| 5,256,661 A | 10/1993 | Horn | 514/248 |
| 5,258,042 A | 11/1993 | Mehta | |
| 5,271,543 A | 12/1993 | Grant et al. | |
| 5,292,053 A | 3/1994 | Bilotti et al. | |
| 5,304,220 A | 4/1994 | Maginot | |
| 5,324,447 A | 6/1994 | Lam et al. | |
| 5,330,503 A | 7/1994 | Yoon | |
| 5,333,773 A | 8/1994 | Main et al. | |
| 5,336,233 A | 8/1994 | Chen | |
| 5,348,259 A | 9/1994 | Blanco et al. | |
| 5,366,462 A | 11/1994 | Kaster et al. | |
| 5,366,473 A | 11/1994 | Winston et al. | |
| 5,387,235 A | 2/1995 | Chuter | |
| 5,395,030 A | 3/1995 | Kuramoto et al. | |
| 5,397,345 A | 3/1995 | Lazarus | 623/1 |
| 5,397,355 A | 3/1995 | Marin et al. | 623/12 |
| 5,403,333 A | 4/1995 | Kaster et al. | |
| 5,456,714 A | 10/1995 | Owen | |
| 5,478,354 A | 12/1995 | Tovey et al. | |
| 5,489,295 A | 2/1996 | Piplani et al. | |
| 5,522,834 A | 6/1996 | Fonger et al. | |
| 5,549,619 A | 8/1996 | Peters et al. | |
| 5,554,162 A | 9/1996 | DeLange | |
| 5,562,690 A | 10/1996 | Green et al. | |
| 5,562,728 A | 10/1996 | Lazarus et al. | |
| 5,620,452 A | 4/1997 | Yoon | |
| 5,634,936 A | 6/1997 | Linden et al. | |
| 5,695,504 A | 12/1997 | Gifford, III et al. | |
| 5,707,380 A | 1/1998 | Hinchliffe et al. | |
| 5,709,335 A | 1/1998 | Heck | |
| 5,720,776 A | 2/1998 | Chuter et al. | |
| 5,732,872 A | 3/1998 | Bolduc | |
| 5,755,775 A | 5/1998 | Trerotola et al. | |
| 5,755,777 A | 5/1998 | Chuter | |
| 5,797,933 A | 8/1998 | Snow et al. | 606/151 |
| 5,833,698 A | 11/1998 | Hinchliffe et al. | |
| 5,839,639 A | 11/1998 | Sauer et al. | 227/175.1 |
| 5,843,164 A | 12/1998 | Frantzen et al. | |
| 5,843,170 A | 12/1998 | Ahn | |
| 5,868,760 A | 2/1999 | McGuckinns et al. | |
| 5,868,763 A | 2/1999 | Spence et al. | 606/153 |
| 5,879,380 A | 3/1999 | Kalmann et al. | |
| 5,881,943 A | 3/1999 | Heck et al. | |
| 5,904,697 A | 5/1999 | Gifford, III et al. | |
| 5,906,607 A | 5/1999 | Taylor et al. | |
| 5,927,284 A | 7/1999 | Borst et al. | |
| 5,931,842 A | 8/1999 | Goldsteen et al. | |
| 5,951,576 A | 9/1999 | Wakabayashi | 606/151 |
| 5,976,159 A | 11/1999 | Bolduc et al. | 606/142 |
| 5,976,176 A | 11/1999 | Webb, II | |
| 5,976,178 A | 11/1999 | Goldsteen et al. | |
| 6,015,378 A | 1/2000 | Borst et al. | |
| 6,019,722 A | 2/2000 | Spence et al. | |
| 6,032,672 A | 3/2000 | Taylor | |
| 6,036,702 A | 3/2000 | Bachinski et al. | 606/153 |
| 6,051,007 A | 4/2000 | Hogendijk et al. | |
| 6,063,021 A | 5/2000 | Hossain et al. | |
| 6,066,148 A | 5/2000 | Rygaard | |
| 6,071,235 A | 6/2000 | Furnish et al. | |
| 6,074,416 A | 6/2000 | Berg et al. | |
| 6,080,175 A | 6/2000 | Hogendijk | |
| 6,095,997 A | 8/2000 | French et al. | |
| 6,110,187 A | 8/2000 | Donlon | |
| 6,110,188 A | 8/2000 | Narciso, Jr. | |
| 6,113,588 A | 9/2000 | Duhaylongsod et al. | |
| 6,139,492 A | 10/2000 | Vierra et al. | |
| 6,152,937 A | 11/2000 | Peterson et al. | |
| 6,165,196 A | 12/2000 | Stack et al. | |
| 6,176,864 B1 | 1/2001 | Chapman | |
| 6,190,353 B1 | 2/2001 | Makower et al. | |
| 6,193,734 B1 | 2/2001 | Bolduc et al. | |
| D440,304 S | 4/2001 | Morales | |
| 6,241,741 B1 | 6/2001 | Duhaylongsod et al. | |
| 6,391,036 B1 * | 5/2002 | Berg et al. | 606/151 |
| 6,485,496 B1 | 11/2002 | Suyker et al. | 606/153 |
| 6,602,263 B1 | 8/2003 | Swanson et al. | 606/153 |
| 6,616,675 B1 | 9/2003 | Evard et al. | |
| 6,702,829 B2 | 3/2004 | Bachinski et al. | |
| 2002/0183769 A1 | 12/2002 | Swanson et al. | 606/153 |

FOREIGN PATENT DOCUMENTS

| | | |
|---|---|---|
| DE | 19542 733 A1 | 11/1979 |
| DE | 195 42 733 A1 | 11/1995 |
| EP | 0 119 688 | 9/1984 |
| EP | 0 384 647 | 8/1990 |
| EP | 0419 660 | 3/1991 |
| EP | 0 539 237 A1 | 10/1992 |
| EP | 0 637 454 | 2/1995 |
| EP | 137685 | 4/1995 |
| EP | 0 689 806 | 1/1996 |
| EP | 0 712 614 | 5/1996 |
| EP | 0 820 724 B1 | 7/1997 |

| | | |
|---|---|---|
| EP | 0 820 725 B1 | 7/1997 |
| EP | 0 885 595 A1 | 6/1998 |
| FR | 1518083 | 12/1968 |
| GB | 935490 | 9/1959 |
| GB | 2038692 | 7/1980 |
| GB | 2108418 | 5/1986 |
| NL | 7711347 | 4/1979 |
| SU | 995765 | 2/1983 |
| SU | 1097301 | 6/1984 |
| WO | WO 89/08433 | 9/1989 |
| WO | WO 95/17127 | 6/1995 |
| WO | 96/10375 | 4/1996 |
| WO | 96/14808 | 5/1996 |
| WO | 98/02099 | 1/1998 |
| WO | WO 98/19608 | 5/1998 |
| WO | WO 98/19618 | 5/1998 |
| WO | WO 98/19629 | 5/1998 |
| WO | WO 98/19630 | 5/1998 |
| WO | WO 98/19631 | 5/1998 |
| WO | WO 98/19632 | 5/1998 |
| WO | WO 98/19634 | 5/1998 |
| WO | WO 98/19732 | 5/1998 |
| WO | WO 98/47430 | 10/1998 |
| WO | WO 98/5027 | 12/1998 |
| WO | WO 98/55027 | 12/1998 |
| WO | WO 99/21491 | 5/1999 |
| WO | WO 99/38454 | 8/1999 |
| WO | WO 00/27313 | 5/2000 |
| WO | 00/53104 | 9/2000 |
| WO | 00/74579 | 12/2000 |

OTHER PUBLICATIONS

Berggren et al., "Clinical Experience with UNILINK 3M Precise Microvascular Anastomotic Device," Scand J Plast Reconstr Hand Surg, 1993;27:35-39.

Calafiore, A.m., "Early Clinical Experience With a New Sutureless Anastomotic Device for Proximal Anastomosis of the Saphenous Vein to the Aorta," The Journal of Thoracic and Cardiovascular Surgery, vol. 121, No. 5, pp. 854-858, May 2001.

Cooper et al., "Development of the Surgical Stapler with Emphasis on Vascular Anastomosis," NY Acad. Sci, 1963; 25:365-377.

Eckstein, f.s., et al., Sutureless Mechanical Anastomosis of a Saphenous Vein Graft to a Coronary Artery With a New Connector Device, The Lancet, pp. 931-932, vol. 357, Mar. 24, 2001.

Gentili et al., "A Technique for Rapid Non-suture Vascular Anastomosis," Can J Neuro Sci, 1987;14(1):92-95.

Goetz et al., "Internal Mammary-coronary Artery Anastomosis: A Nonsuture Method Employing Tantalum Rings," J Thorac Card Surg, 1961;41(3):378-386.

Gottlob et al., "Anastomoses of Small Arteries and Veins by Means of Bushings and Adhesive," J Card Surg. 1968;9: 337-341.

Guyton et al., "A Mechanical Device for Sutureless Aorta-Saphenous Vein Anastomosis," Ann Thorac Surg. 1979;28: 342-345.

Holt et al., "A New Method for Microvascular Anastomosis: Report of Experimental and Clinical Research," The American Surgeon, 1992;58(12):722-727.

Holt et al., "A New Technique for End-to-end Anastomosis of Small Arteries," Surg Forum, 1960;11:242.

Inokuchi, "A New Type of Vessel-suturing Apparatus," AMA Arch Surg, 1958;77:954-957.

Inokuchi, "Stapling Device for End-to-side Anastomosis of Blood Vessles," Arch Surg, 1961;82:27-31.

Kirsch et al., "A New Method for Microvascular Anastomosis: Report of Experimental and Clinical Research," American Surgeon, 1992;58:722-727.

Kirsh et al., "A New Technique for End-to-end Anastomosis of Small Arteries," Surgical Forum, 1960;11:242-243.

Lanzetta et al., "Long-term Results of 1 Millimeter Arterial Anastomosis Using the 3M Precise Microvascular Anastomotic System," Microsurgery, 1992;13:313-320.

Li et al., "End-to-side-anastomosis in the Dog Using the 3M Precise Microvascular Anastomotic System: A Comparative Study," J Reconstruct Microsurg, 1991;7(4):345-350.

Miller, "The Russian Stapling Device," Acad Sci, 1963;25: 378-381.

Nakayama et al., "A Simple New Apparatus for Small Vessel Anastomosis (free autograft of the sigmoid included)," Surgery, 1962;52(6):918-931.

Narter et al., "An Experimental Method for Nonsuture Anastomosis of the Aorta," Surg Gyne & Obs, 1964;632-361.

Nazari et al., "Expandable Prosthesis for Sutureless Anastomosis in Thoracic Aorta Prosthetic Substitution", European Journal of Cardiothoracic Surgery, vol. 10, No. 11, 1996, pp1003-1009.

Olearchyk, "Vasilil I. Kolesov-A Pioneer of Coronary Revascularization by Internal Mammary-coronary Artery Grafting," J Thorac Surg, 1988;96(1):13-18.

Ragnarsson et al., "Arterial End-to-side Anastomosis with the UNILINK System," Ann Plastic Surg, 1989;22(3):405-415.

Ragnarsson et al, "Microvenous End-to-side Anastomosis: An experimental Study Comparing the UNILINK System and Sutures," J Reconstruct Microsurg, 1989;5(3):217-224.

Rohman et al., Chapter IX-Cardiovascular Technique, "Double Coronary Artery-internal Mammary Artery Anastomoses, Tantalum Ring Technique," Surg Forum, 1960;11;263-243.

J. Rosch et al., "Modified Gianturco Expandable Wire Stents in Experimental and Clincial Use", Annals of Radiology, 1998, 31,2, pp. 100-104.

Vogelfanger et al., "A Concept of Automation in Vascular Surgery: A Preliminary Report on a Mechanical Instrument for Arterial Anastomosis." Can J Surg, 1958;58:262-265.

Ann Thorac Surg, Assessment Of Patented Coronary End-To-Side Anastomotic Devices Using Micromechanical Bonding, Department of Design, Engineering and PRoductin, Delft University of Technology, The Netherlands, Jul. 2000; 70(1) :218-21.

Werker et al, "Review of Faciitated Approaches To Vascular Anastomosis Surgery", Department of Plastic, REconstructive and Hand Surgery, University Hospital Utrecht, Utrecht, the Netherlands, 1997: 63:5127.

* cited by examiner

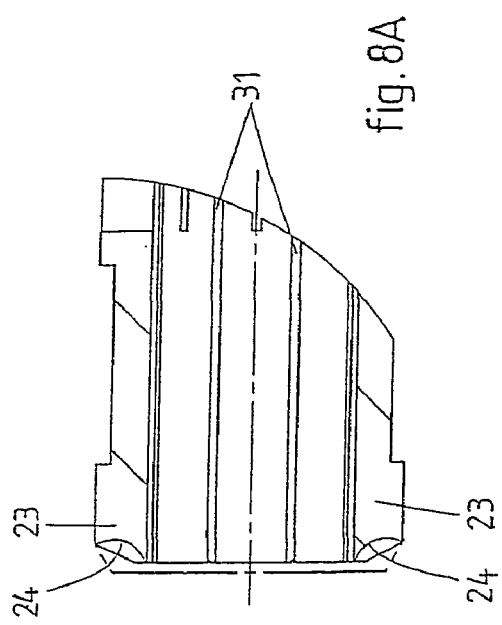
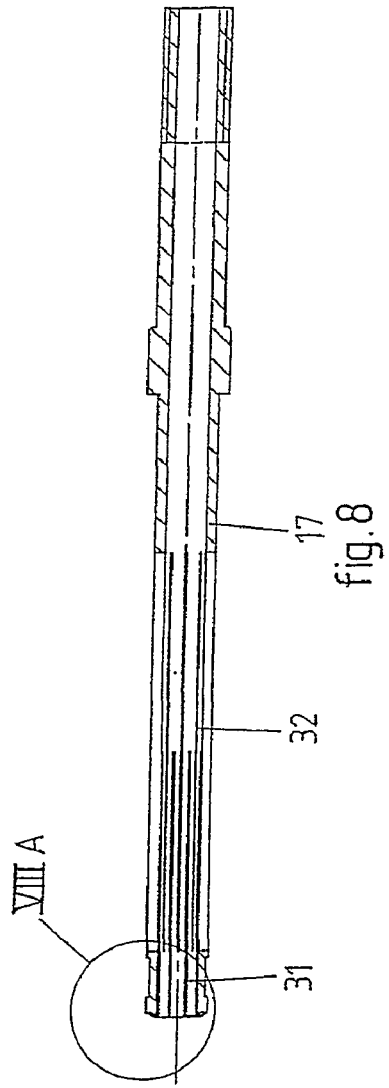
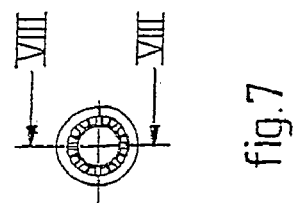

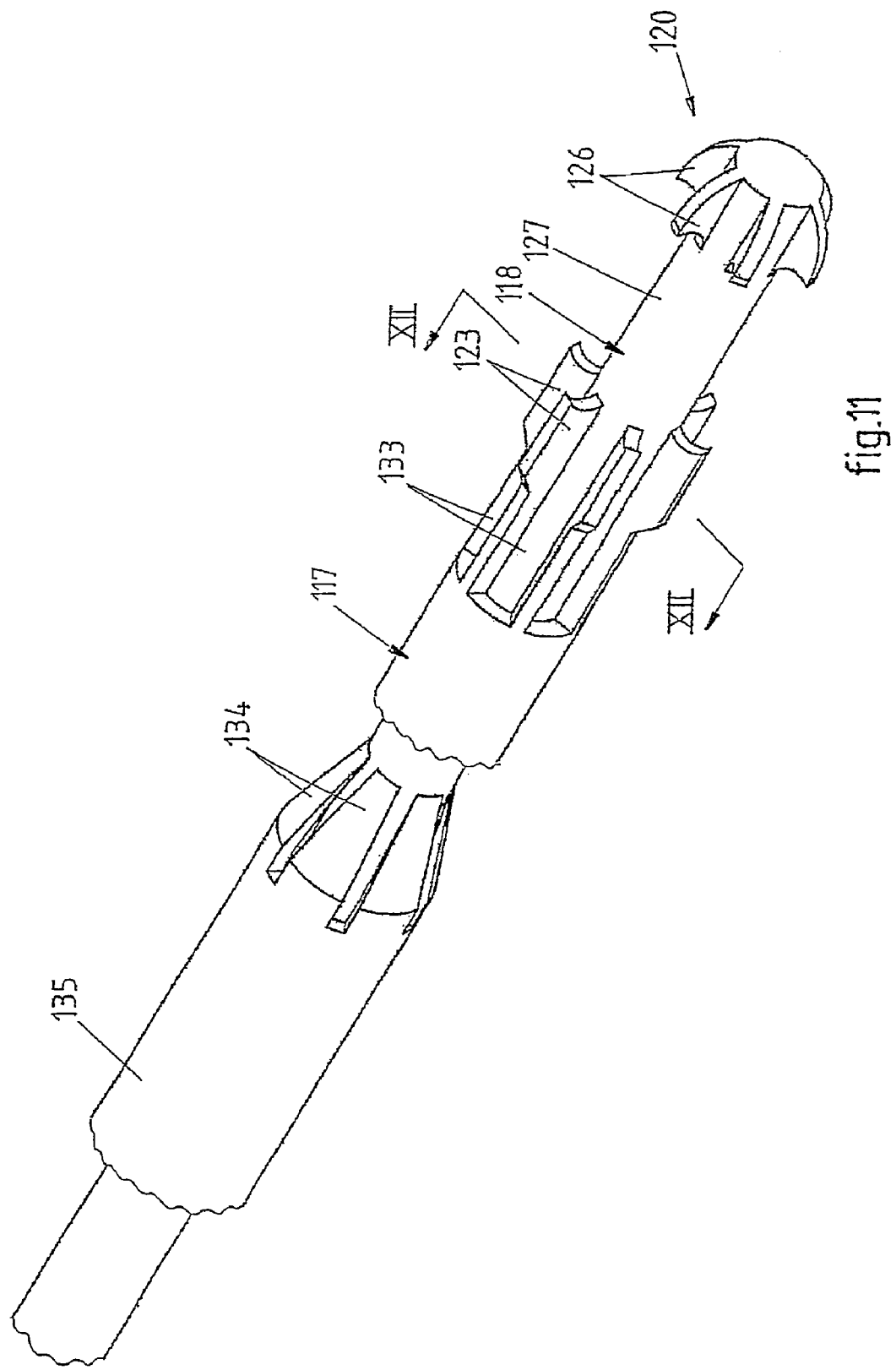

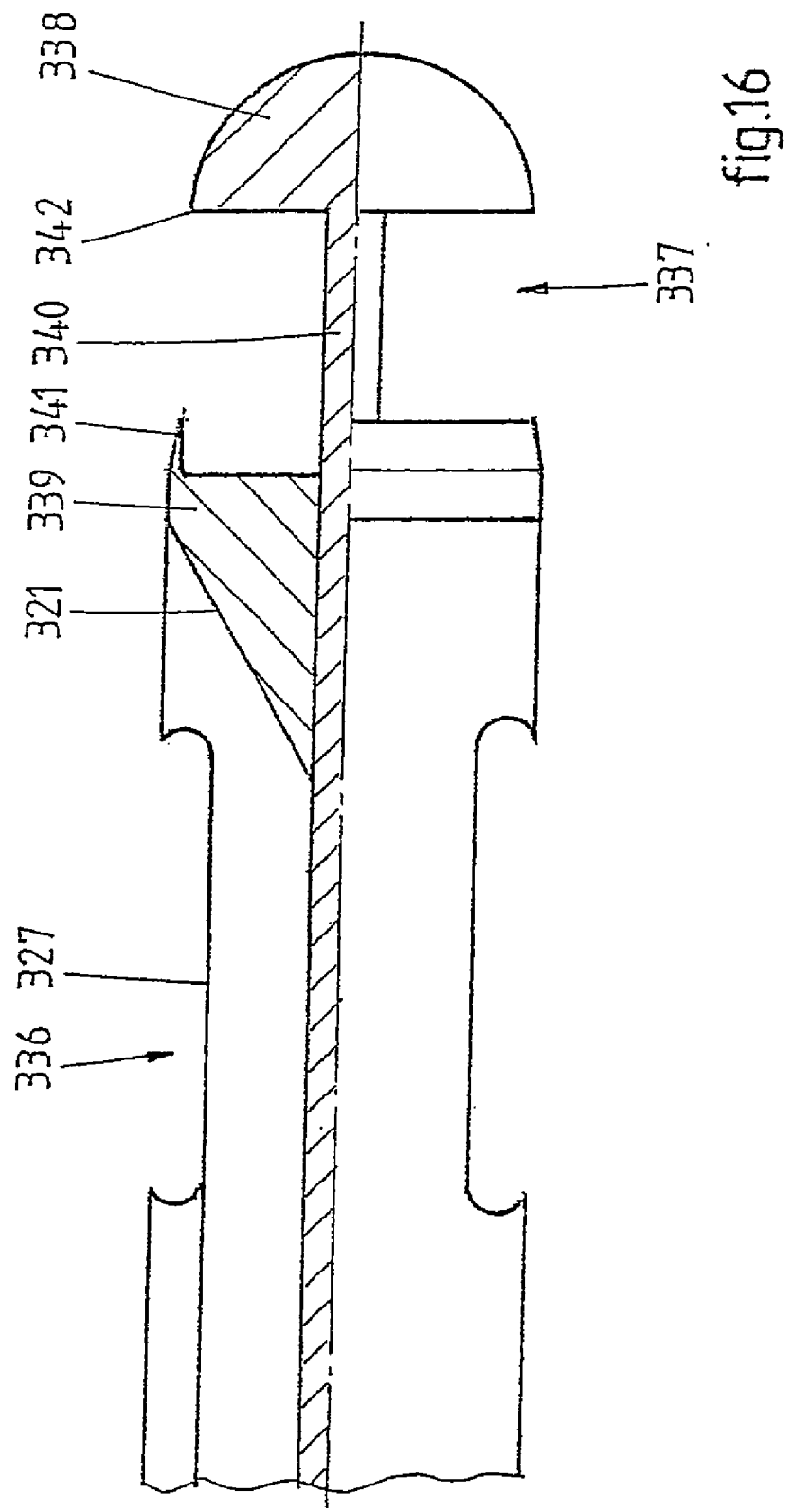

DEFORMABLE CONNECTOR FOR MECHANICALLY CONNECTING HOLLOW STRUCTURES

BACKGROUND OF THE INVENTION

1. Field of the Invention

The present invention relates to a connector and applicator for mechanically connecting hollow structures, in particular small blood vessels, through so called anastomoses. Such means may for example be used when making a bypass past narrowings or occlusions of arteries caused by arteriosclerosis.

2. Background Art

One such connector and applicator are known from WO-A-99/21491 of applicants. This document discloses several embodiments of connectors which are made up of an annular member and circumferentially spaced joining means for holding the vessel walls together in order to make the joint between the vessels. The connectors as disclosed are suitable both for end-to-side and side-to-side anastomoses.

The object of the present invention is to further improve the connector and applicator for making mechanical connections between hollow structures.

BRIEF SUMMARY OF THE INVENTION

To obtain this object, the present invention provides a connector for mechanically connecting hollow structures, in particular small vessels, comprising:

an annular member of deformable material, said member having a center line and being adapted to be permanently deformed by expansion from a first size in a starting position in which it is delivered to a desired anastomoses site, to a second, larger size in a joining position in which it connects the hollow structures, and circumferentially spaced means for joining abutting walls of the hollow structures together, said means including staple-like elements being adapted to be permanently deformed from a starting position in which the connector is delivered to a desired site, to a joining position in which they engage the hollow structures to connect them, said staple-like elements having at least two free ends and being attached to the annular member between its free ends and being tapered from the annular member towards their free ends.

This connector according to the invention has various advantages. The expandability of the annular member is advantageous because, as a result, the size of the connector is small during delivery, whereas the size of the annular member can be adapted to the size of the vessels on the site of the anastomosis. The staple-like elements are very suitable for holding together adjacent vessel walls of the vessels to be connected. Due to the tapering, the predictability of the plastic deformation, which is required to close the staples, is improved. If the staples should be curved according to a certain curvature, the deformation will start at the tips and progress towards the annular member, which leads to a predictable deformation. The tapering can take various forms. The staple-like elements may for example be conically or wedge-shaped towards the free ends. Preferably, the radial thickness of the staple-like elements is diminished towards the respective free ends, but also the width may be tapered.

In a preferred embodiment, the staple-like elements are substantially straight and parallel to the center line of the annular member. With this arrangement, the connector can have a minimum diameter which facilitates easy handling during an operation. From this straight starting position, the staple-like elements can be deformed either to a C-shape to form a perfect or overlapping circle, or to a B-shape or an overlapping B-shape.

In order to further increase the predictability of the deformation phase of the staple-like elements, the staple-like elements may be provided with extreme tips which are preformed into the anticipated curve of the deformation to the joining position.

It is not necessary that the portions of the staple-like elements on either side of the point of attachments to the annular member are mirror shaped. The length, thickness and slope towards the free ends can be varied to accommodate required bending characteristics or vessel wall thicknesses.

It is preferred to make the connector according to the invention from one piece of material, preferably metal, for example stainless steel 316L or titanium. Connectors which are sufficiently small for use in coronary artery bypass surgery can be manufactured from one piece of metal by using a combination of cutting with a lathe and subsequently using laser techniques or electric erosion techniques. In this way, the connector is made directly in 3D. Alternatively, 2D-techniques like photo-etching and electroplating can be used to make 2D pieces out of thin, flat material. These can be converted into 3D, either by forcing a 2D shape into 3D, or by bending and welding together the beginning and end of the 2D shape.

An easily expandable annular member is obtained if the annular member is made up from a continuous elongated piece of material having a sinusoidal pattern meandering about a circle line through the annular member. In this case, the staple-like elements are preferably formed at an apex of the sinusoidal pattern.

In order to increase the maximum size of the annular member in the joining position, it is preferred to have the main plane of the annular member at an angle to the center line of the annular member.

Due to this feature, the orifice area of the anastomosis can be increased without increasing the size of the connector and applicator, which is limited by the diameter of the hollow structures through which the applicator is inserted. The above feature results in an elliptical anastomosis with an increased orifice area as compared to a circular anastomosis, while the size of the applicator can remain unchanged. In case the main plane of the annular member is at an angle of for example 45°, the area is increased by a factor $\sqrt{2}=1.41$. Practically the staple-like elements of the connector will remain parallel to the center line of the applicator and connector.

The present invention also includes an applicator for delivering and deploying a connector for mechanically connecting hollow structures, comprising:

a shank-like element;

a head formed at a distal end of the shank-like element, said head being adjustable in such a manner that the annular member and the staple-like elements of the connector are deformed from the starting position to the joining position when said adjusting takes place, said head including an inner member and an outer member which are longitudinally slidable and include longitudinally opposite anvil formations which are movable to and for upon relative sliding movements of the inner and outer members in order to deform the staple-like elements to theirs joining position;

wherein both the inner and outer members are expandable to deform the connector to the joining position.

Due to the expandability of both the inner and outer members, it is possible to minimize the radial dimensions of the applicator. It is now possible to make the head of the applicator smaller than the radial size of the connector in the joining position, since the outer member of the head of the applicator is enabled to expand together with the connector.

A simple manner to obtain the expandability of the inner and outer members is to slit or cut them in axial direction. Preferably, the outer member includes at least first slits and second slits, said first slits are arranged at an end of the outer member which forms part of the head and extends between the anvil formations, said second slits being spaced from said and of the outer member, and alternate with the first slits and are configured in overlapping arrangement.

Due to this configuration of the slits or cuts, the radial as well as the tangential stiffness of the delicate material between the slits is increased. This further assists in diminishing the dimensions of the head of the applicator.

Another advantageous feature to minimize the radial dimensions of the head is the feature that the anvil formations, on their sides facing each other, have curved surfaces dictating the deformation of the staple-like elements, said curved surfaces being formed to such an extent that they terminate at an angle to the longitudinal axis of the head which is slightly beyond 90°, for example 91°–120°.

These "low profile" anvil formations make the applicator head as slender as possible, but nonetheless allow for a predictable bending of the staple-like elements of the connector.

An alternative applicator according to the invention comprises a shank-like element, and a head formed at a distal end of the shank-like element, said head being adjustable in such a manner that the annular member and the staple-like elements of the connector are deformed from the starting position to the joining position when said adjusting takes place. The head includes an inner member and an outer member which are longitudinally slidable and include longitudinally opposite anvil formations which are movable to and from upon relative sliding movements of the inner and outer members in order to deform the staple-like elements to their joining position. The head further includes an expansion member comprising wedges adapted to slide underneath the annular member.

In this embodiment of the applicator according to the invention, the expansion of the annular member of the connector is effected by the wedges of the expansion member which slide underneath the annular member and thereby urging the annular member outwardly.

One way of enabling the wedges to slide underneath the annular member is to make the expansion member slidable relative to the inner and outer members, and in this embodiment it is advantageous if the wedges are interleaved with the anvil formations, since the head of the applicator can then be made as small as possible.

In this embodiment of the applicator, the simplest design thereof is obtained if the staple-like elements are first deformed to their joining position, whereafter the annular member is expanded by the wedges of the expansion member. In that case it is not necessary to make the outer member expandable and in a preferred embodiment it is even possible to expand the annular member of the connector and remove it from the head of the applicator in distal direction over the anvil formations of the inner member in a continued operation.

In another embodiment of the applicator according to the invention, the head includes not only an anastomosis portion which is adjustable in such a manner that the annular member and the joining elements of the connector are deformed from the starting position to the joining position when said adjusting takes place, but also a punching portion distally of the anastomosis portion and including two relatively movable parts configured to cause a punching action on a wall of the hollow structure and to catch or trap a punched-out part of said wall.

With such applicator it is possible to both cut a hole in the vessel wall in order to enable the applicator to enter the vessel, and to perform the anastomosis with the same instrument. This simplifies the procedure and reduces time and cost.

The invention further includes a method of delivering and deploying a connector for mechanically connecting hollow structures. This method comprises the steps of:
   providing a connector for joining adjacent walls of the hollow structures,
   providing an applicator for said connector, said applicator including cutting means,
   making an arteriotomy in the wall of one of the hollow structures,
   inserting the cutting means of the applicator partly into said one of the hollow structures through the arteriotomy, so as to cut a hole in the wall,
   advancing the applicator up to a desired position,
   deploying the connector by means of the applicator so as to connect the walls of the hollow structures.

BRIEF DESCRIPTION OF THE SEVERAL VIEWS OF THE DRAWINGS

The invention will further be described with reference to the drawings showing embodiments of the invention by way of example.

FIG. 7 is an axial view of the outer member of the applicator of FIG. 4, on a larger scale.

FIG. 8 is a sectional view of the outer member of FIG. 7 along the plane VIII—VIII.

FIG. 11 is a very schematic perspective view of members forming the head of an alternative embodiment of the applicator according to the invention.

FIG. 16 is a very schematic, partly cut-away side view of the head of a further embodiment of an applicator according to the invention, FIGS. 1–3 show an embodiment of a connector for mechanically connecting hollow structures, in particular small blood vessels, such as coronary arteries. The connector is specially designed for making a side-to-side anastomosis but may also be used or adapted to make other connections, for example an end-to-side anastomoses or other joints.

The connector as shown comprises an annular one and a plurality of joining means in the form of staple-like elements 2 spaced around the circumference of the annular member 1. The annular member and staple-like elements are preferably formed from one piece of material, preferably metal such as stainless steel 316L or titanium.

Figure 1:
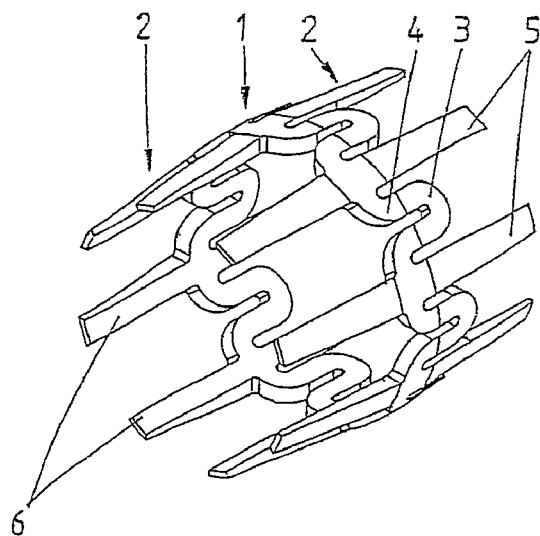
FIG. 1 is a perspective view of an embodiment of the connector according to the invention.
Figure 2:
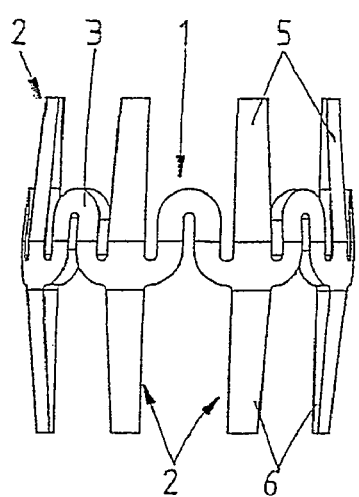
FIG. 2 is a view of the connector of FIG. 1 in radial direction.
Figure 3:
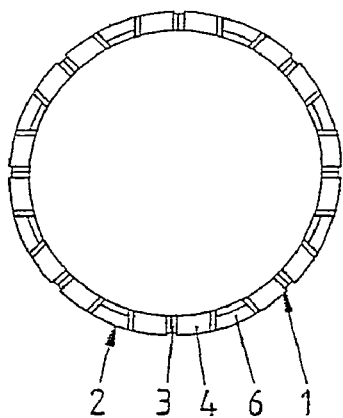
FIG. 3 is a view of the connector of FIG. 1 in axial direction.

The annular member as shown in FIGS. 1–3 comprises a continuous elongated element having a sinusoidal pattern meandering about a circle line through the annular member. The alternating waves 3 and 4 of the pattern have a different wave length in order to accommodate the staple-like elements 2 which are formed at each wave 4, at the apex thereof. The meandering pattern of the annular member 1 creates the expandability of the annular member by widening the meanders or waves of the pattern thereby increasing the diameter of the annular member 1. The deformation of the annular member 1 is plastically, so that the annular member 1 will retain its shape after expansion.

The configuration of the annular member 1 may vary within a broad range, including the length of the annular member 1. The term annular also covers tubular members.

The staple-like elements 2 comprise two staple portions 5, 6 which extend from the point of attachment to the annular member 1 in opposite directions. In the embodiment shown, both staple portions 5, 6 are aligned and are substantially each other's mirror image, but it should be kept in mind that that need not be the case. Instead thereof, the length, thickness and slope towards the free ends of the staple portions 5,6 can be varied to accommodate required bending characteristics or vessel wall thicknesses.

As is shown in FIGS. 1–3, in which the connector is shown in its starting position in which it is delivered to the anastomosis site, the staple-like elements are substantially straight and extend parallel to the center axis of the annular member. The staple portions 5, 6 are slightly tapered towards their free ends, both in radial thickness and in circumferential width. The tapering is on the outer side of the staple portions 5, 6, whereas the radial inner side of the staple portions 5, 6 extends parallel to the center axis. The circumferential sides of the staple portions 5, 6 are inclined relative to a radial plane through the center of the staple portions 5, 6 such that the width of a staple-like element 2 is smaller on the radial inner side than on the radial outer side. If desired, the extreme tips of the staple portions 5, 6 may be preformed into the anticipated curve, to increase the predictability of the deformation of the staple portions 5, 6. The waves 3 may also be slightly tapered, i.e. having a diminishing thickness in axial direction in the same manner as the adjacent staple portions 5.

FIGS. 4–10 show an embodiment of the applicator according to the invention. The applicator includes a main body 7, a grip 8 extending downwardly therefrom on the rear end, a control lever 9 pivotally connected to the front end of the main body 7 and extending downwardly, and a stroke limiter 10 pivotally attached to the lower end of the control lever 9 and slidably connected to the lower end of the grip 8. A pin slot connection 11 between the stroke limiter 10 and the grip 8 determines the maximum stroke of the control lever 10. The control arm may be locked in position by locking the stroke limiter 10 to the grip 8. The control lever 9 is pivotally connected to an intermediate pivot 12 in order to provide a long lever arm 13 and a short lever arm 14. The end of the short lever arm 14 is pivotally connected to a sliding block 15, the sliding motion being guided and limited through a bolt 16.

Attached to the sliding block 15 is an outer tube member 17 and attached to the main body 7 is an inner tube member 18. The inner and outer members 17, 18 together form a shank-like element and on the free end thereof a head 20 adapted to accommodate a connector in order to deliver it to the anastomosis site and to deploy it into a joining position. FIGS. 7 and 8/8a show the outer tube member 17 and FIGS. 9 and 10/10a show the inner tube member 18 in more detail. Inside of the inner tube member is an expansion core connected to an expansion control means 22.

The outer member 17 is provided on its distal end with proximal anvil formations or anvils 23 having a curved surface 24 facing, in a assembled condition, corresponding curved surfaces 25 of distal anvil formations or anvils 26 provided on the distal end of the inner member 18. The number of distal and proximal anvils 23, 26 is equal to the number of staple-like elements 2 of each connector, in this case 8. The anvils 23, 26 are distributed around the circumference of the inner and outer members 17, 18 in the same manner as the staple-like elements on the connector, in this case equally spaced around the circumference. The inner member 18 is provided with a seat 27, proximal of the anvils 26, to accommodate the connector during delivery and in this starting position of the applicator and connector, the inner and outer members 17, 18 have such relative position that the connector is positioned between adjacent anvils 23 and 26 of the inner and outer members 17, 18, with each staple-like element 2 being aligned with respective anvils 23, 26.

In order to be able to expand the connector which is seated on the seat 27 of the inner member 18, this inner member is slitted with cuts or slits 28 extending from the distal end of the inner member 18 a distance in proximal direction. The length of the slits is such that the tongues left between the slits 28 may undergo a sufficient radial deflection to expand the connector to a sufficient extent. The length of the slits may for example be 5–10 times the diameter of the inner member 18. The lumen 29 through the inner tube member 18 has a flaired end part 30, in which the diameter of the lumen is increased in distal direction, for example at an angle of approximately 30°. This end part 30 is adapted to accommodate the tapered end part of the expansion core 21, so that when the expansion core 21 is retracted in proximal direction by the expansion control means 22, the tapered end part urges the tongues between the slits 28 of the inner tube member 18 outwardly so that the connector present on the seat 27 is expanded.

As is shown in FIGS. 7 and 8, also the outer tube member 17 is slitted. The outer tube member 18 comprises first slits 31 extending from the distal end of the outer tube member 17 a distance in proximal direction, and partly overlapping second slits 32 which alternate with the first slits 31 and extend from a position intermediate the ends of the first slits 31 to a position proximal of the first slits 31. The total length of the first and second slits may for example be 5–10 times the diameter of the outer member 18. Due to this slit arrangement, the radial and tangential strength of the outer member 17 is increased.

The operation of the applicator and connector as shown and described before is as follows.

Figure 4:
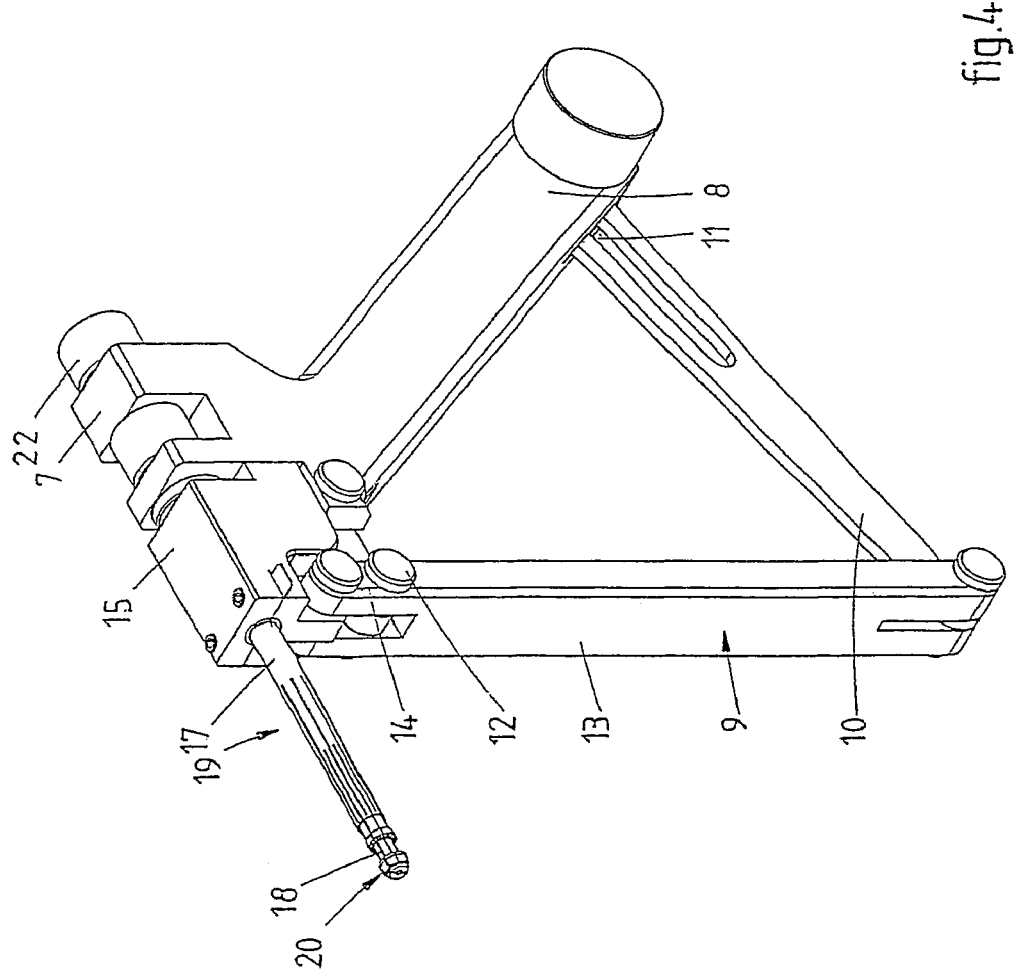
FIG. 4 is a perspective view of an applicator for use with the connector of FIGS. 1–3, on a smaller scale.
Figure 6:
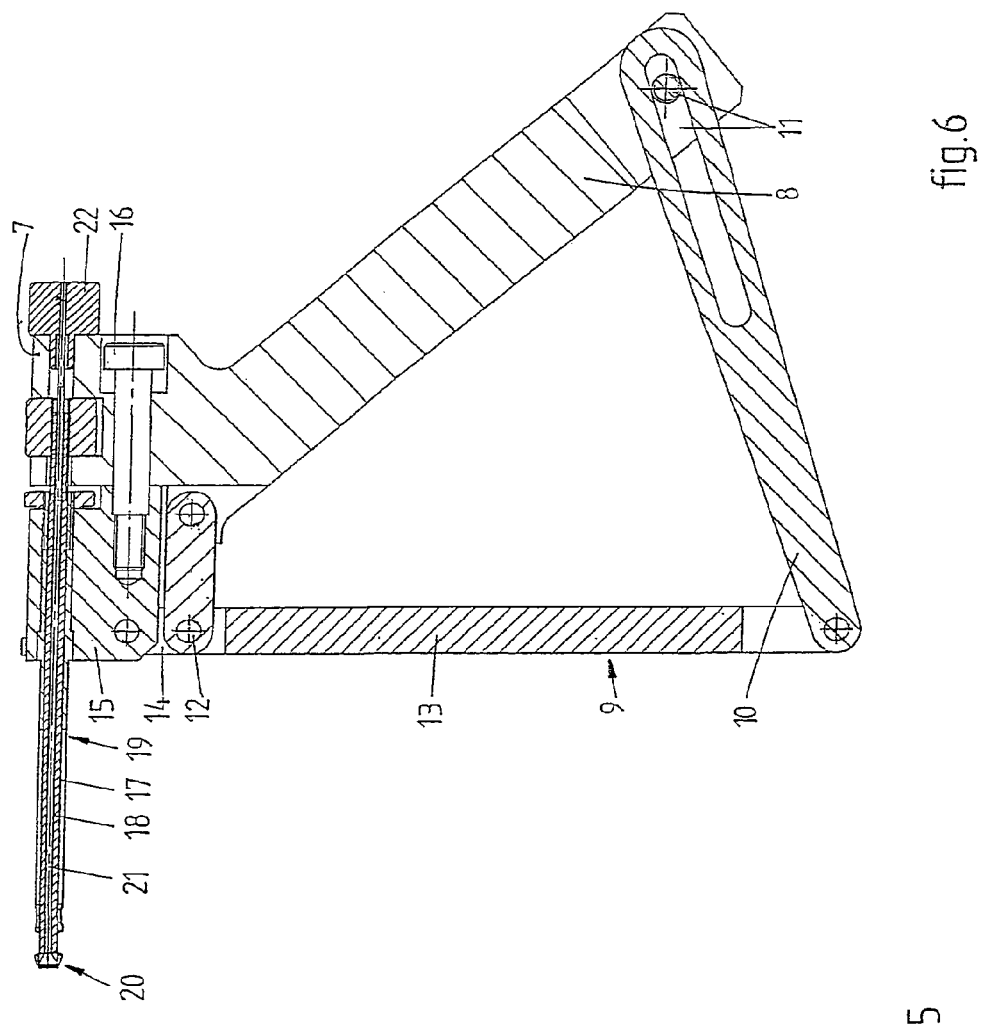
FIG. 6 is a sectional view of the applicator of FIG. 4, along the plane VI—VI in FIG. 5.
Figure 5:
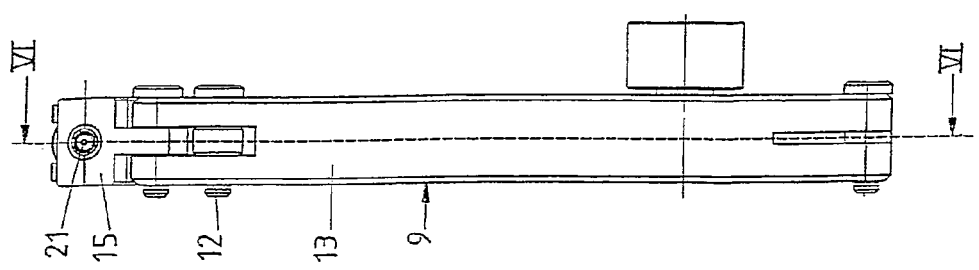
FIG. 5 is a front view of the applicator of FIG. 4.
Figure 10A:
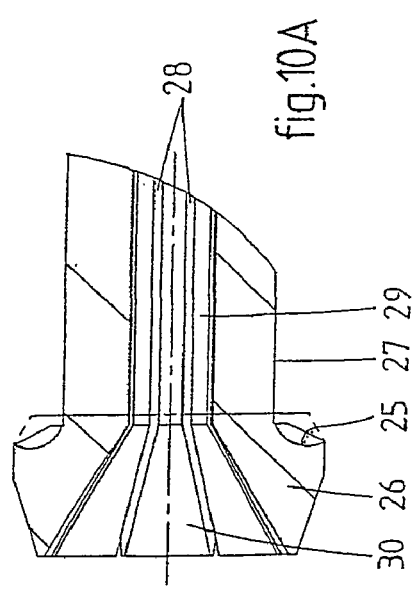
FIG. 10 is a sectional view of the inner member of FIG. 9, taken along the line X—X.
Figure 10:
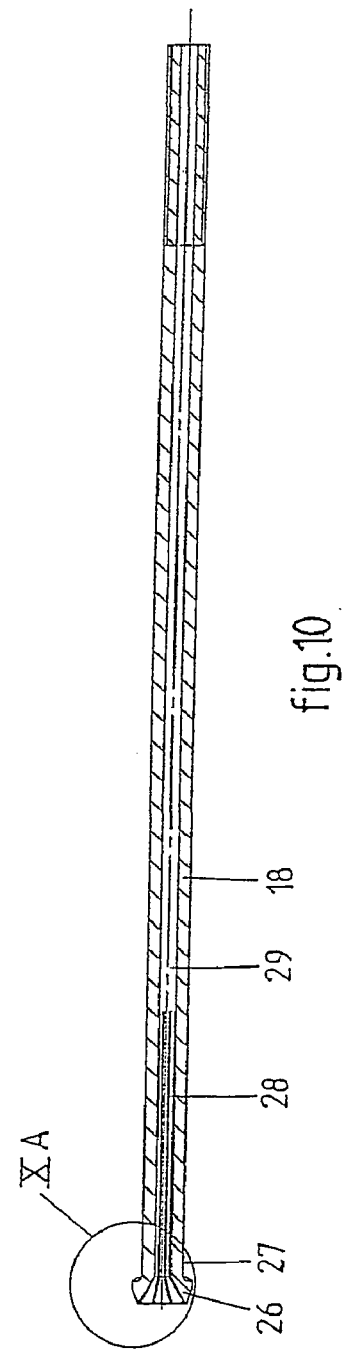
Figure 9:
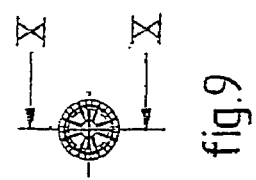
FIG. 9 is an axial view of the inner member of the applicator of FIG. 4, on a larger scale.

The shank-like element 19 with a connector positioned on the seat 27 of the head 20 is inserted into one of the vessels to be joined and is delivered to the site where the anastomosis should be accomplished. The control lever 9 is in the position as shown in FIG. 4. If the head 20 and therefore the connector is positioned correctly with respect to vessel walls which are positioned around the connector, the expansion control means 22 is actuated to retract the expansion core 21 so as to expand the inner member 18 and therefore the annular member 1 of the connector. Since the outer tube member 17 is also slitted, it is possible for the outer member 17 to follow the expansion of the inner member. As a result the anvil formations 23 and 26 remain substantially in their relative opposite positions, so that, after expansion of the annular member 1 of the connector, it is possible to activate the anvils 23, 26 in order to deform the staple-like elements 2 of the connector.

The activation of the anvils 23, 26 is effected by sliding the outer tube member 17 in distal direction along the inner member 18 so as to bring the opposite anvils 23, 26 closer to each other thereby engaging the initially straight staple portions 5, 6 of the staple-like elements 2 and upon a further approaching movement of anvils 23, 26 the staple portions 5, 6 follow the curvature of the curved surfaces 24, 25 of the anvils 23, 26. The curved surfaces 24, 25 are shaped as circular segments, which extend through approximately 91–120°, and preferably 115°, which is sufficient to allow a full deformation of each staple portion 5, 6. Depending on the lateral and radial curvature of the surfaces 24, 25, staple portions 5, 6 are deformed either to a C-shape to form a perfect or overlapping circle, or to a B-shape or an overlapping B-shape. After both the annular member 1 and the staple-like elements 2 are deformed into their joining position, the staple portions 5, 6 clamp the vessel walls of adjacent vessels between each other thereby effecting an anastomosis. The expansion core 21 can then be moved back to the starting position so that both the inner and outer members are collapsed into their unexpanded condition in which the outer dimensions of the distal anvil formations 26 is smaller than the inner dimension of the anular member 1 of the connector in expanded condition, so that the applicator can be withdrawn from within the annular member 1 of the connector so as to be removed from the vessel and the body of the patient.

Figure 13A:
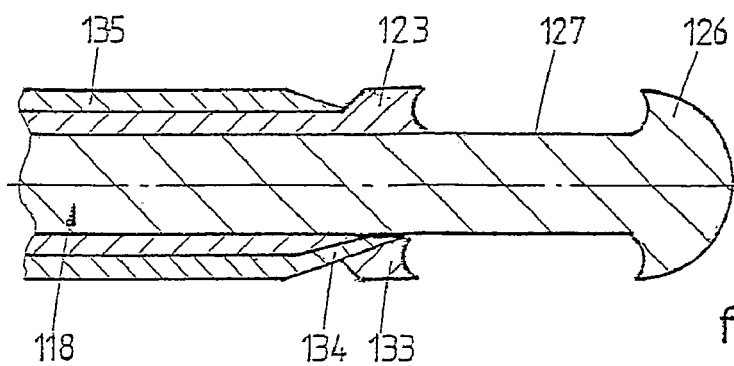
FIGS. 13A–13C are longitudinal sectional views of the applicator head of FIG. 11, in three different positions during deployment of the connector.
Figure 13:
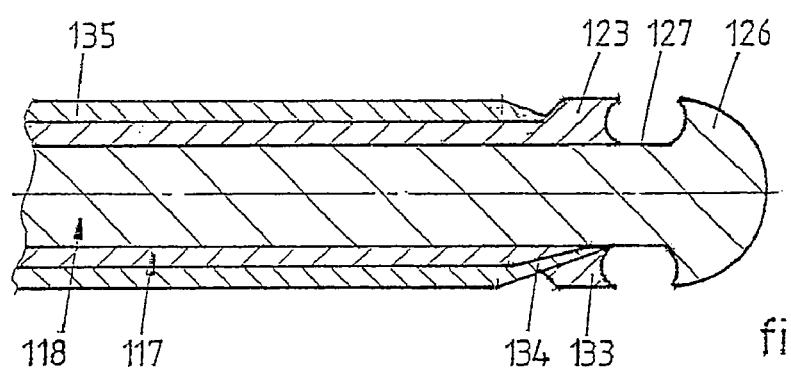
Figure 12:
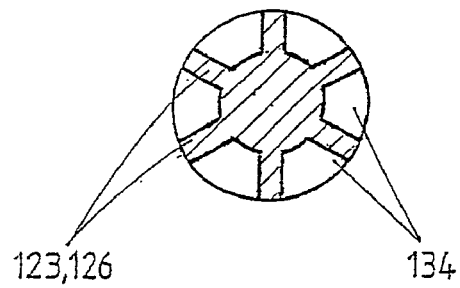
FIG. 12 is a sectional view along the line XII—XII in FIG. 11.

FIGS. 11–13 show an alternative embodiment of an applicator according to the invention, which may be used to deliver and deploy the connector of FIGS. 1–3. FIGS. 11–13 show a head 120 of the shank-like element of the applicator, said head being formed by an outer member 117 and an inner member 118. The inner member has a seat 127 and distal anvils 126. The outer member 17 has proximal anvils 123 between each two adjacent anvils 123. There is created a gap 133 of sufficient axial length to accommodate wedges 134 and provided on the distal end of an expansion member 135. The expansion member 135 fits slidingly around the outer member 117 such that the wedges are positioned in their respective gap 133 between adjacent anvils 23 or distally thereof. The wedges 134 extend inwardly from the tube-like expansion member 135 up to the outer diameter of the inner member 118, so that the extreme tips of the wedges 134 engage the outer surface of the inner member 118. The extreme tips of the wedges 134 are sharp so as to facilitate them to slide underneath the annular member 1 so as to engage the annular member 1 and upon a distal sliding movement of the expansion member 135 relative to the inner and outer members 117, 118, the annular member 1 of the connector 1 is expanded by the wedges 134.

Figure 13C:
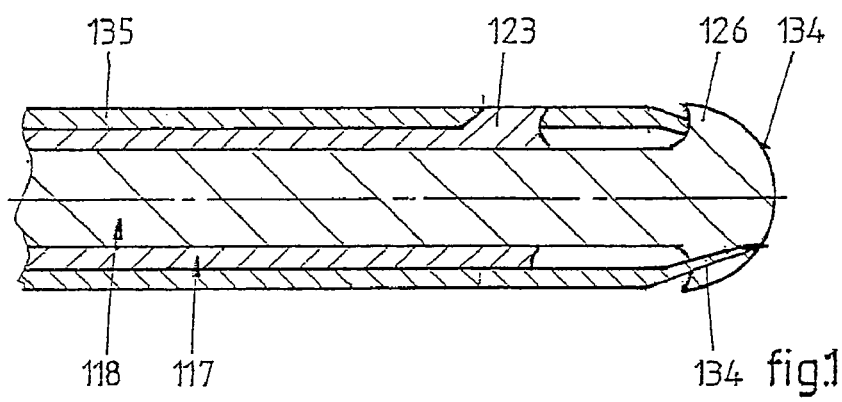

In this embodiment, the deformation of the staple-like elements 2 take place before the expansion of the annular member 1, so that the inner and outer members 117, 118 are actuated first in order to close the staple-like elements 2 (FIGS. 13a–13b), whereafter the expansion member 135 is moved in distal direction so as to expand the annular member 1 and urge it over the anvil formations 126 so as to remove the connector from the head 120 of the applicator (FIG. 13c).

Figure 14:
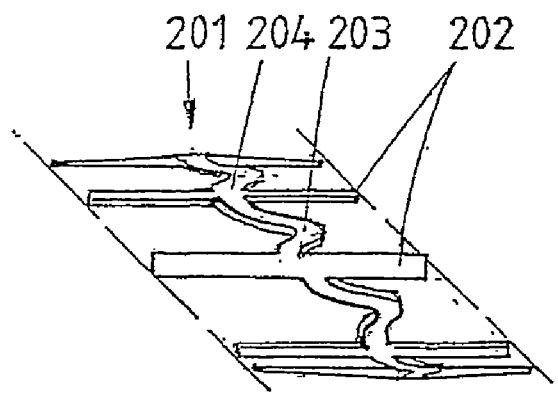
FIG. 14 is a very schematic side view of an alternative embodiment of the connector according to the invention.

FIG. 14 shows an alternative embodiment of a connector for connecting the walls of hollow structures, in particular small vessels through an anastomosis. The connector includes an annular member 201 having staple-like elements 202. The annular member 201 and staple-like elements 202 are very similar to those of the embodiment of FIG. 1, with the exception of one aspect. The connector has a center line C which is in the center of the lumen through the connector. The connector also includes a main plane M which extends through the middle of the annular member. In this embodiment, the center line C is at an angle to the main plane M, which is different from 90°. In the present case, the angle within the plane of the drawing is circa 45°. The staple-like elements 202 extend parallel to the center line C.

The reason for using this embodiment is as follows. The maximum size-(orifice area) of the anastomosis is limited by the size of the connector and applicator, which in turn is limited by the diameter of the vessel through which the applicator and connector are inserted. In order to increase the orifice area of the anastomosis, the plane of stapling can be tilted, for example 45°. After expansion to the joining position, this results in an elliptical anastomosis with an increased orifice area (in this case $\sqrt{2}=1.41$) as compared to a circular anastomosis, whereas the size of the applicator remains unchanged. Thus, it is possible to create bigger anastomoses through a blood vessel having a particular size.

In practice, the staple-like elements 202 of the connector will remain parallel to the central axis of the applicator, while the meandering ring will extend at an angle of 45° to a plane which is perpendicular to the center line C. The meandering waves 203, 204 are, however, within the circular cylinder around the center line C.

Figure 15:
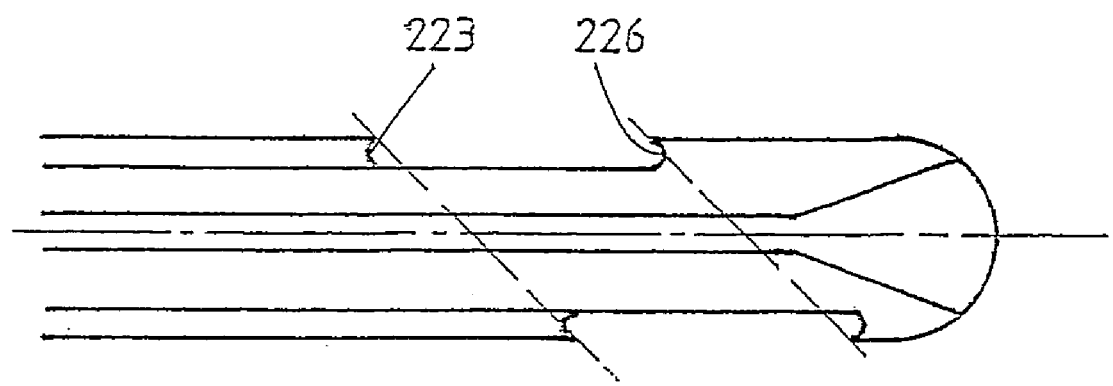
FIG. 15 is a very schematic side view of the head of an applicator for delivering and deploying the connector of FIG. 14.

FIG. 15 shows a head 220 of an applicator to deliver and deploy the connector according to FIG. 14. As is shown, the position of the proximal and distal anvil formations 223, 226 are adapted to the relative position of the staple-like elements 202.

FIG. 16 shows a further embodiment of an applicator for making anastomoses. In anastomosis procedures, it is often desirable to punch out a hole in the vessel wall at the site of the anticipated anastomosis. This is especially the case when doing the proximal anastomosis in CABG (coronary artery bypass grafting) operations, where for example a piece of saphenous vein graft has to be connected to the ascending aorta, which is a big (30 mm) artery and has a significant wall thickness (2–3 mm). However, on a much more delicate scale, punching out a small hole for the distal anastomosis on the coronary artery itself could also prove to be advantageous.

The embodiment of the applicator according to FIG. 16 has means to punch out a hole in the vessel wall incorporated in the head thereof. FIG. 16 shows that the head of this embodiment includes an anastomosis portion 336 and a punching portion 337. This punching portion 337 is positioned distally of the anastomoses portion 336. The punching portion 337 includes two relatively movable parts, a distal part 338 and a proximal part 339. The distal part 338 is mounted on a core 340 running through the head and shank and is adapted to be operated in order to move axially with respect to the proximal part 339. On their sides facing each other, both parts 338 and 339 are provided with cutting means, including a circular knife 341 on the proximal portion 339 and a counter edge 342. The circular knife 341 is sized to accurately slide over the distal part 338 while performing a cutting action in co-operation with the edge 342. The distal front of the distal part 338 is rounded for easy insertion into an arteriotomy. Alternatively, this rounded front can be replaced by a knife or a conical shape, ending in a sharp point. This configuration permits creating an arteriotomy, punching out a hole and securing the anastomosis with one instrument and requiring only one instrument insertion. To punch the hole this rounded front of the distal part 338 is inserted into the arteriotomy, subsequently this distal part 338 is pulled against the circular knife 341 of the proximal part 339. A circular piece of vessel wall is then cut out and remains trapped between and inside the distal and proximal parts 338, 339 which together enclose this vessel wall piece. This entrapment is important since loose tissue fragments can embolize.

Subsequently, the applicator is pushed further inwardly so that the anastomosis portion 336 is brought in line with the vessel walls to be joined. The expansion mechanism of the anastomosis portion 336 is activated by further retracting the core 340 and distal part 338 in order to push the expansion core 321 (formed on the proximal part 339) in proximal direction with respect to the anastomosis portion 336 so as to expand the seat 327 where the connector is positioned. The further operation of the applicator is similar to that of the embodiment of FIGS. 4–10.

This embodiment has the unique feature of being capable to punch a hole and secure the anastomosis during one instrument insertion. Because it is not necessary to remove the applicator between these two manipulations, there is very limited blood loss and maximum control. This makes the applicator very suitable for making proximal anastomoses on the aorta in port access CABG.

Alternatively, the punch mechanism could be replaced by a single, linear knife, which makes a linear arteriotomy. The applicator is than advanced through this arteriotomy and deforms it to a more circular shape.

From the foregoing it is clear that the present invention provides a connector, applicator and method for mechanically connecting small blood vessels and the like in a simple, reliable and efficient manner.

The punch mechanism could also be replaced by a simple, circular knife. A pointed wire with a simple retaining mechanism like a hook, extending distally to the circular knife would puncture the vessel wall before cutting and would hold the piece of vessel wall after cutting to prevent it from embolizing in the patient.

The invention is not restricted to the embodiments shown in the drawing and described herein before and can be varied within the scope of the accompanying claims.

We claim:

1. A connector for mechanically connecting hollow structures, in particular small vessels, comprising:
    an annular member of deformable material, said annular member being permanently deformable by expansion via plastic deformation from a first size in a starting position in which the connector is delivered to a desired anastomosis site, to an annular member having a second, larger size in a joining position in which the connector connects the hollow structures,
    joining elements circumferentially spaced about said annular member for joining abutting walls of the hollow structures together, said joining elements comprising staple-like elements which are permanently deformable from a starting position in which the connector is delivered to a desired anastomosis site, to a joining position in which said staple-like elements engage the hollow structures to thereby cause the connector to connect the hollow structures, each said staple-like element being attached to the annular member, and comprising at least two staple portions extending from said location of said attachment between each said staple-like element and said annular member to free ends of each said staple portion, at least part of each said staple portion being tapered in a direction corresponding to a direction from the location of attachment between each said staple-like element and said annular member towards the free end of said staple portion.

2. The connector as claimed in claim 1, wherein each said staple portion tapers to at least a lesser radial thickness.

3. The connector as claimed in claim 1, wherein a center line of each of the staple-like elements is disposed substantially within a radial plane of the annular member.

4. The connector as claimed in claim 2, wherein the staple-like elements are substantially straight in their starting position.

5. The connector as claimed in claim 3, wherein the staple portions of the staple-like elements have extreme tips which, in the starting position, are curved to approximate an anticipated curve of said tips resulting from deformation of said staple-like elements from the starting position to the joining position.

6. The connector as claimed in claim 1, wherein the connector is made from one piece of material.

7. The connector as claimed in claim 1, wherein the staple portions of at least some of the staple-like elements are configured differently on opposite sides of the point of attachment between the staple-like elements and the annular member.

8. The connector as claimed in claim 1, wherein the annular member is made from a continuous, elongate piece of material having a sinusoidal pattern meandering about a circumferential line through the main plane of the annular member.

9. The connector as claimed in claim 8, wherein each said staple-like element is located at an apex of the sinusoidal pattern.

10. The connector as claimed in claim 1, wherein said tapering of at least one said staple portion provides predetermined bending characteristics to said at least one staple portion.

11. The connector as claimed in claim 10, wherein said tapering of said at least one staple portion causes said at least one staple portion to permanently deform to a C-shape in said joining position.

12. The connector as claimed in claim 10, wherein said tapering of said at least one staple portion causes said at least one staple portion to permanently deform to a C-shape forming a circle in said joining position.

13. The connector as claimed in claim 10, wherein said tapering of said at least one staple portion causes said at least one staple portion to permanently deform to a C-shape forming overlapping circles in said joining position.

14. The connector as claimed in claim 10, wherein said tapering of said at least one staple portion causes said at least one staple portion to permanently deform to a B-shape in said joining position.

15. The connector as claimed in claim 10, wherein said tapering of said at least one staple portion causes said at least one staple portion to permanently deform to an overlapping B-shape in said joining position.

16. The connector as claimed in claim 1, wherein the tapering of said staple portions is located on a radially outer side of said staple portions.

17. The connector as claimed in claim 1, wherein the tapering of each said staple portion results in a reduction of a radial thickness of a part of said staple portion, relative to a radial thickness of another part of said staple portion.

18. The connector as claimed in claim 1, wherein the tapering of each said staple portion results in a reduction of a circumferential width of a part of said staple portion, relative to a circumferential width of another part of said staple portion.

19. The connector as claimed in claim 1, wherein the tapering of each said staple portion results in a reduction of both a radial thickness and a circumferential width of a part of said staple portion, relative to a radial thickness and a circumferential width, respectively, of another part of said staple portion.

20. The connector as claimed in claim 6, wherein a laser is employed to make the connector.

21. The connector as claimed in claim 6, wherein electric erosion is employed to make the connector.

22. The connector as claimed in claim 6, wherein the connector is fabricated by first making a two-dimensional shape from the single material, and then forcing the two-dimensional shape into a desired three-dimensional shape.

23. The connector as claimed in claim 22, wherein the two-dimensional shape is made by photo-etching.

24. The connector as claimed in claim 22, wherein the two-dimensional shape is made by electroplating.

25. The connector as claimed in claim 6, wherein the connector is fabricated by first making a two-dimensional shape from the single material, and then bending and welding portions of the two-dimensional shape to create a desired three-dimensional shape.

26. The connector as claimed in claim 22, wherein the two-dimensional shape is made by photo-etching.

27. The connector as claimed in claim 22, wherein the two-dimensional shape is made by electroplating.

28. The connector as claimed in claim 1, wherein each said staple portion is tapered from a position proximate the annular member.

29. A connector for mechanically connecting hollow structures, in particular small vessels, comprising:

an annular or tubular member of deformable material, said annular member having a center line, and said annular member being adapted to be permanently deformed from a first size in a starting position in which the connector is delivered to a desired site, to an annular member having a second, larger size in a joining position in which the connector connects the hollow structures, joining elements circumferentially spaced about said annular or tubular member for joining abutting walls of the hollow structures together, said joining elements including staple-like elements which are permanently deformable by plastic deformation from a starting position in which the connector is delivered to a desired site, to a joining position in which said staple-like elements engage the hollow structures to thereby cause the connector to connect the hollow structures, each said staple-like element being attached to the annular member proximate to a center of said staple-like element and extending in a direction substantially parallel to the center line of the annular member when said connector is in said starting position, and wherein pairs of said staple-like elements are aligned with one another on said annular member.

\* \* \* \* \*